US006759035B2

(12) United States Patent
Horwitz (10) Patent No.: US 6,759,035 B2
(45) Date of Patent: Jul. 6, 2004

(54) METHOD TO PREVENT GRAFT REJECTION USING TGF-BETA TO INDUCE T SUPPRESSOR CELLS

(75) Inventor: David A. Horwitz, Santa Monica, CA (US)

(73) Assignee: University of Southen California, Los Angeles, CA (US)

( * ) Notice: Subject to any disclaimer, the term of this patent is extended or adjusted under 35 U.S.C. 154(b) by 0 days.

(21) Appl. No.: 09/833,526

(22) Filed: Apr. 11, 2001

(65) Prior Publication Data

US 2002/0006392 A1 Jan. 17, 2002

Related U.S. Application Data

(60) Provisional application No. 60/196,446, filed on Apr. 11, 2000.

(51) Int. Cl.[7] .................. A61K 45/00; G01N 33/567
(52) U.S. Cl. .................. 424/85.1; 424/85.2; 424/93.71; 435/7.24; 435/70.3
(58) Field of Search ............................. 435/7.24, 70.3; 424/93.71, 85.1

(56) References Cited

U.S. PATENT DOCUMENTS

| 6,228,359 B1 | 5/2001 | Horwitz |
| 6,358,506 B1 | 3/2002 | Horwitz |
| 6,406,696 B1 | 6/2002 | Bluestone |
| 6,447,765 B1 | 9/2002 | Horwitz |

FOREIGN PATENT DOCUMENTS

| WO | 93/17698 A1 | 9/1993 |
| WO | WO 97/42324 A1 | 11/1997 |
| WO | WO 99/25366 A1 | 5/1999 |
| WO | WO 99/48524 * | 9/1999 |
| WO | WO 00/66158 A2 | 11/2000 |
| WO | WO 01/16296 A2 | 3/2001 |

OTHER PUBLICATIONS

Halverson et al, Blood 90(5): 2089–96, Sep. 1997.*
Bonig et al, Scand J Immunol 50:612–618, Dec. 1999.*
Mysliwietz et al, Blood 80(10):2661-7, Nov. 1992, Abstract.*
Garderet et al, Transplantation 67(1): 124–30; Jan. 1999.*
Early et al, Clin Exp Immunol 116(3): 527–33, Jun. 1999.*
Heitger et al, Blood 90(2): 850–57, Jul. 1997.*
Chen et al, J Immunology 161: 909–918, 1998.*
Rosario et al, Blood 93(10): 3558–3564, May 1999.*
Anasetti et al., "Treatment of acute graft–versus–host disease with a nonmitogenic anti–CD3 monoclonal antibody", Transplantation 54:844–851 (1992).
Asano M, et al., "Autoimmune disease as a consequence of developmental abnormality of a T cell subpopulation." J Exp Med. Aug. 1, 1996;184(2):387–96.

Barker et al., "Identification of multiple and distinct CD8+ T cell suppressor activities: dichotomy between infected and uninfected individuals, evolution with progression of disease, and sensitivity to gamma irradiation," J Immunol 156:4476–4483 (1996).
Blazar et al., Both CD4+ and CD8+ T Cells Can Cause Accelerated GVHD Lethality in the Presence of High In Vivo Doses of Exogenous Ill10: Role of Interfereon Gamma (IFNγ) in GVHD Induction, Blood 88:247 (1996) (abstract).
Blazar et al., "FK506 inhibits graft–versus–host disease and bone marrow graft rejection in murine recipients of MHC disparate donor grafts by interfering with mature peripheral T cell expansion post–transplantation", J. Immunol 153:1836–1846 (1994).
Blazar et al., "Murine recipients of fully mismatched donor marrow are protected form lethal graft–versus–host disease by the in vivo administration of rapamycin but develop an autoimmune–like syndrome", J. Immunol 151:5726–5741 (1993).
Blazar et al., "Recent advances in graft–versus–host disease (GVHD)", Immunol Rev 157:79–90 (1997).
Bonini et al., HSY–TK gene transfer into donor lymphocytes for control of allogeneic graft–versus–leukemia, Science 276:1719–1724 (1997).
Border et al., "Transforming growth factor–beta in disease: the dark side of tissue repair," J Clin Invest 90:1–7 (1992).
Boussiotis et al., "B7 but not intercellular adhesion molecule–1 costimulation prevents the induction of human alloantigen–specif tolerance," J Exp Med 178:1753–1763 (1993).
Chandrasekar, B., et al., "Dietary calorie restriction inhibits transforming growth factor–beta (TGF–beta) expression in murine lupus nephritis", 9th International Congress on Immunology, 848 (1995).
Chavin et al., "Anti–CD2 mAbs Suppress Cytotoxic Lymphocyte Activity by the Generation of Th2 Suppressor Cells and Receptor Blockade," J Immunol 152:3729–3739 (1994).
Chong P. et al. "Inhibition of protein–kinase C in peripheral blood mononuclear cells of patients with systemic lupus erythematosus: effect on spontaneous immunoglobulin production," Autoimmunity, 10:227–231 (1991).
Delgiudice, G., et al., "TGF–beta activity is increased in systemic lupus erythematosus (SLE) and progressive systemic sclerosis (PSS)", Arthritis and Rheumatism vol. 36 (9 Suppl.) p S196(Sep. 1993).
Dumont et al., "Distinct Mechanisms of Suppression of Murine T Cell Activation by the Related macrolides FK–506 and Rapamycin", J. Immunol 144:251–258 (1990).

(List continued on next page.)

Primary Examiner—Christina Chan
Assistant Examiner—Phuong Huynh
(74) Attorney, Agent, or Firm—Robin M. Silva; Renee M. Kosslak; Dorsey & Whitney LLP (57) ABSTRACT

The invention relates to compositions and methods useful for preventing graft rejection in a recipient following organ transplantation.

5 Claims, 7 Drawing Sheets

OTHER PUBLICATIONS

Dupont, B., "Immunology of hematopoietic stem cell transplantation: a brief review of its history", Immunol Reviews 157:5–12 (1997).
Fast, "Generation and characterization of IL–2–activated veto cells", J Immunol 149:1510–1515 (1992).
Fernandes, G., et al., "Calorie restriction delays autoimmune murine lupus by differentially modulating oncogenes and TGF–beta–1 expression", 9th International Congress on Immunology., 848 (1995).
Fowler et al., "Donor CD4–enriched cells of Th2 cytokine phenotype regulate graft–versus–host disease without impairing allogeneic engraftment in sublethally irradiated mice", Blood 84:3540–3549 (1994).
Gao Q, et al., "CD4+CD25+ cells regulate CD8 cell anergy in neonatal tolerant mice." Transplantation. Dec. 27, 1999;68(12): 1891–7.
Goldman et al., "Bone marrow transplantation for chronic myelogenous leukemia in chronic phase. Increased risk for relapse associated with T–cell depletion", Ann Intern Med 108:806–814 (1988).
Gratama et al., "Treatment of Acute Graft–Versus–Host Disease With Monoclonal Antibody OKT3. Clinical results and effect on circulating T lymphocytes", Transplantation 38(5):469–474 (1984).
Gray et al., "Activated Natural Killer Cells Can Induce Resting B Cells to Produce Immunoglobulin." Arthritis & Rheumatism, 37(9)suppl:S378 (1994).
Gribben et al., "Complete blockade of B7 family–mediated costimulation is necessary to induce human alloantigen–specific anergy: a method to ameliorate graft–versus–host disease and extend the donor pool", Blood 97:4887–4893 (1996).
Hahn, B.H., Dubois'Lupus Erythematosus, 5th Ed. (1997), pp. 69–76 (D.J. Wallace et al. eds., Williams and Wilkins, Baltimore).
Herve et al., "Treatment of Corticosteroid Resistant Acute Graft–Versus–Host Disease by In Vivo Administration of Anti–Interleukin–2 Receptor Monoclonal Antibody (B–B10)", Blood 75(4):1017–1023 (1990).
Hirohata et al., "Role of II–2 in the generation of CD4+ suppressors of human B cell responsiveness", J Immunol 142:3104–3112 (1989).
Hirokawa et al., "Human resting B lymphocytes can serve as accessory cells for anti–CD2–induced T cell activation", J. Immunol. 149:1859–1866, 1992.
Hiruma et al., "Effects of anti–CD3 monoclonal antibody on engraftment of T–cell–depleted bone marrow allografts in mice: host T–cell suppression, growth factors, and space", Blood 79:3050–3058 (1992).
Horwitz DA, et al., "Decreased production of interleukin–12 and other Th1–type cytokines in patients with recent–onset systemic lupus erythematosus." Arthrtis Rheum. May 1998;41(5)838–44.
Horwitz, D. A., et al., "The immunoregulatory effects of NK cells: the role of TGF–β and implications for autoimmunity", Immunology Today, vol. 18(11):538–542 (Nov. 1997).
Horwitz, D.A., Dubois'Lupus Erythematosus, 5th Ed. (1997), pp. 155–194 (D.J. Wallace et al. eds., Williams and Wilkins, Baltimore).

Huggins, M. L., et al., "Modulation of the Autoimmune Response in Lupus Mice by Oral Administration of Attenuated Salmonella typhimurium Expressing the IL–2 and TGF–β Genes", Annals of New York Acad. of Sciences, vol. 815:499–502 (1997).
Jackson AL, et al., "Restricted expression of p55 interleukin 2 receptor (CD25) on normal T cells." Clin Immunol Immunopathol. Jan. 1990;54(1):126–33.
Kanegane H, et al., "A novel subpopulation of CD45RA+ CD4+ T Cells expressing IL–2 receptor alpha–chain (CD25) and having a functionally transitional nature into memory cells." Int Immunol. Dec. 1991;3(12):1349–56.
Kinter et al., "Interleukin 2 induces CD8+ T cell–mediated suppression of human immunodeficiency virus replication in CD4+ T cells and this effect overrides its ability to simulate virus expression", Proc. Natl. Acad. Sci. USA 92:10985–10989 (1995).
Klinman DM, et al., "Quantitation of IgM– and IgG–secreting B cells in the peripheral blood of patients with systemic lupus erythematosus." Arthritis Rheum. Nov. 1991;34(11):1404–10.
Krenger et al., "Effects of exogenous interleukin–10 in a murine model of graft–versus–host disease to minor histocompatibility antigens", Transplantation 58:1251–1257 (1994).
Krenger et al., "Polarized type 2 alloreactive CD4+ and CD8+ donor T cells fail to induce experimental acute graft–versus–host disease", J Immunol 153;585–593 (1995).
Linker–Israeli M., et al., "CD8+ lymphocytes from patients with systemic lupus erythematosus sustain, rather than suppress, spontaneous polyclonal IgG production and synergize with CD4+ cells to support autoantibody synthesis." Arthritis Rheum. Aug. 1990;33(8):1216–25.
Lucas et al., "The development of cellular immunity to Epstein–Barr virus after allogeneic bone marrow transplantation", Blood 87:2594–2603 (1996).
Martin et al., "Effects of in vitro depletion of T cells in HLA–identical allogeneic marrow grafts", Blood 66:664–672 (1985).
Martin et al., "Effects of treating marrow with a CD3–specific immunotoxin for prevention of acute graft–versus–host disease", Bone Marrow Transplant 3:437–444 (1989).
Martin, "Overview of Marrow Transplantation Immunology", in Bone Marrow Transplantation (eds. Forman et al.) pp. 16–21, Boston, Blackwell Scientific Publications (1994).
Martin, P.J. et al., "Treatment of Acute Graft–Versus–Host Disease with Anti–CD3 Monoclonal Antibodies," Am Jour Kidney Disease 11(2):149–152 (1988).
Massague J., "The transforming growth factor–beta family." Annu Rev Cell Biol. 1990;6:597–641.
Massague, "Receptors for the TGF–bata family", Cell 69:1067–1070 (1992).
Morris, "Prevention and treatment of allograft rejection in vivo by rapamycin: molecular and cellular mechanisms of action", Ann NY Acad Sci 685:68–72 (1993).
Murphy et al, "The potential role of NK cells in the separation of graft–versus–tumor effects from graft–versus–host disease after allogeneic bone marrow transplantation," Immunol Rev 157:167–176 (1997).
Ohtsuka, K., et al., "Decreased Production of TGF–β by Lymphocytes from Patients with Systemic Lupus Erythematosus", J. Immunol. 160:2539–2545 (1998).

Oswald, et al., "IL–10 Synergizes with IL–4 and Transforming Growth Factor–Beta to inhibit macrophage Cytotoxic Activity," J Immunology 148(11):3578–3582 (1992).

Papiernik M, et al., "T cell deletion induced by chronic infection with mouse mammary tumor virus spares a CD25–positive, IL–10–producing T cell population with infectious capacity." J Immunol. May 15, 1997;158(10):4642–53.

Patterson et al., "Graft rejection following HLA matched T–lymphocyte depleted bone marrow transplantation", Br J Haematol 63:221–230 (1986).

Powrie F, et al., "A critical role for transforming growth factor–beta but not interleukin 4 in the suppression of T helper type 1–mediated colitis by CD45RB(low) CD4+ T cells." J Exp Med. Jun. 1, 1996; 183(6):2669–74.

Read S, et al., "Cytotoxic T lymphocyte–associated antigen 4 plays an essential role in the function of CD25(+)CD4(+) regulatory cells that control intestinal inflammation." J Exp Med. Jul. 17, 2000;192(2):295–302.

Rodt, H., "Anti–lymphocytic antibodies and marrow transplantation. 3. Effect of heterologous anti–brain antibodies on acute secondary disease in mice", Eur. J. Immunol 4:25–29 (1974).

Sakaguchi S, et al., "Organ–specific autoimmune diseases induced in mice by elimination of T cell subset. I. Evidence for the active participation of T cells in natural self–tolerance; deficit of a T cell subset as a possible cause of autoimmune disease." J Exp Med. Jan. 1, 1985;161(1):72–87.

Shivakumar S, et al., "T cell receptor alpha/beta expressing double–negative (CD4–/CD8–) and CD4+ T helper cells in humans augment the production of pathogenic anti–DNA autoantibodies associated with lupus nephritis." J Immunol. Jul. 1, 1989;143(1):103–12.

Sporn et al., "Some recent advances in the chemistry and biology of transforming growth factor–beta," J Cell Biol 105:1039–1045 (1987).

Storb et al., "Long–term follow–up of a controlled trial comparing a combination of methotrexate plus cyclosporine with cyclosporine alone for prophylaxis of graft–versus–host disease in patients administered HLA–identical marrow grafts for leukemia", Blood 80:560–561 (1992).

Strand, V., "Approaches to the management of systemic lupus erythematosus," Current Opinion in Rheumatology, 9:410–420 (1997).

Sullivan et al., "Chronic Graft–Versus–Host Disease and Other Late Complications of Bone Marrow Transplantation", Semin Hematol 28:250–259 (1992).

Suri–Payer E, et al, "CD4+CD25+ T cells inhibit both the induction and effector function of autoreactive T cells and represent a unique lineage of immunoregulatory cells." J Immunol. Feb. 1, 1998;160(3):1212–8.

Suri–Payer E, et al., "Post–thymectomy autoimmune gastritis: fine specificity and pathogenicity of anti–H/K ATPase–reactive T cells." Eur J Immunol. Feb. 1999;29(2):669–77.

Takahashi T, et al., "Human CD8+ lymphocytes stimulated in the absence of CD4+ cells enhance IgG production by antibody–secreting B cells." Clin Immunol Immunopathol. Mar. 1991;58(3):352–65.

Takahashi T, et al., "Immunologic self–tolerance maintained by CD25+CD4+ naturally anergic and suppressive T cells: induction of autoimmune disease by breaking their anergic/suppressive state." Int Immunol. Dec. 1998;10(12):1969–80.

Taylor, "Antigen specific suppressor T cells respond to cytokines released by T cells", Advances Exp Med Biol 319:125–135 (1992).

Thornton AM and Shevach EM. "CD4+CD25+ immunoregulatory T cells suppress polyclonal T cell activation in vitro by inhibiting interleukin 2 production." J Exp Med. Jul. 20, 1998;188(2):287–96.

Thornton AM and Shevach EM. "Suppressor effector function of CD4+CD25+ immunoregulatory T cells is antigen nonspecific." J Immunol. Jan. 1, 2000;164(1):183–90.

Vallera et al., "Bone marrow transplantation across major histocompatibility barriers in mice. Effect of elimination of T cells from donor grafts by treatment with monoclonal Thy–1.2 plus complement or antibody alone", Transplantation 31:218–222 (1981).

Via et al., "Critical Role of interleukin–2 in the development of acute graft–versus–host disease", International Immunol 5:565–572 (1993).

Wahl SM. "Transforming growth factor beta: the good, the bad, and the ugly." J Exp Med. Nov. 1, 1994;180(5):1587–90.

Weiner HL, et al., "Oral tolerance: immunologic mechanisms and treatment of animal and human organ–specific autoimmune diseases by oral administration of autoantigens." Annu Rev Immunol. 1994;12:809–37.

Zeller, et al., "Ex vivo IL10 and TGF–Beta Act Synergistically to Induce CD4+ Alloantigen–Specific Tolerance Resulting in Diminished Graft–Versus–Host Disease in Vivo," FASEB Journal (Mar. 12, 1999) 12(4)part 1, A6514. Meeting Info: Annual Meeting of the Professional Research Scientists for Experimental Biology. Apr. 17–21 1999.

Dooms, H. et al., "IL–2 and IL–15 direct the outcome of inappropriate CD4+ T cell stimulation towards apoptosis and anergy respectively," European Cytokine Network, 9(3):169 (1998).

Gray et al., "The Role of Transforming Growth Factor β in the Generation of Suppression: an Interaction Between CD8+ T and NK Cells," J Exp Med 180:1937–1942 (1994).

Gray et al., "Generation of an Inhibitory Circuit Involving CD8+ T Cells, IL–2 and NK Cell–Derived TGF–β: Contrasting Effects of Anti–CD2 and Anti–CD3", J Immunol, 160:2248–2254 (1998).

Auchincloss, Hugh Jr., et al, in *Fundamental Immunology* 4th Ed., Paul, W.E. (ed.) Lippincot–Raven: Philadelphia, New York; 1999 pp. 1182–1222.

Betz, M. and Fox, B.S., "Prostaglandin E2 inhibits production of Th1 lymphokines but not of Th2 lymphokines," J Immunol. Jan. 1, 1991;146(1):108–13.

Bucy, R.P. et al., FASEB J. 1995 9:A497 (Abstract).

Cosimi, A.B., et al., "Treatment of acute renal allograft rejection with OKT3 monoclonal antibody," Transplantation. Dec. 1981;32(6):535–9.

Groux, H., et al., "A CD4+ T–cell subset inhibits antigen–specific T–cell responses and prevents colitis," Nature. Oct. 16, 1997;389(6652):737–42.

Jonuleit, H., et al., "Induction of interleukin 10–producing, nonproliferating CD4(+) T cells with regulatory properties by repetitive stimulation with allogeneic immature human dendritic cells," J Exp Med. Nov. 6, 2000;192(9):1213–22.

Kirk, A.D., et al., "CTLA4–Ig and anti–CD40 ligand prevent renal allograft rejection in primates," *Proc Natl Acad Sci U S A*. Aug. 5, 1997;94(16):8789–94.

Koide, J. and Engleman, E.G., "Differences in surface phenotype and mechanism of action between alloantigen–specific CD8+ cytotoxic and suppressor T cell clones," *J Immunol*. Jan. 1, 1990;144(1):32–40.

Lancaster, F., et al., "Anti–idiotypic T cells suppress rejection of renal allografts in rats," *Nature*. May 23–29, 1985;315(6017):336–7.

Langrehr, J.M., et al., "Evidence that nitric oxide production by in vivo allosensitized cells inhibits the development of allospecific CTL," *Transplantation*. Mar. 1992;53(3):632–40.

Larsen, C.P., et al., "Long–term acceptance of skin and cardiac allografts after blocking CD40 and CD28 pathways," *Nature*. May 30, 1996;381(6581):434–8.

Mizuochi, T., et al., "Both L3T4+ and Lyt–2+ helper T cells initiate cytotoxic T lymphocyte responses against allogenic major histocompatibility antigens but not against trinitrophenyl–modified self," *J Exp Med*. Aug 1, 1985;162(2):427–43.

Pearce, N.W., et al., "Specific unresponsiveness in rats with prolonged cardiac allograft survival after treatment with cyclosporine. V. Dependence of CD4+ suppressor cells on the presence of alloantigen and cytokines, including interleukin 2," *Transplantation*. Feb. 1993;55(2):374–80.

Pescovitz, M.D., et al., "Effect of class II antigen matching on renal allograft survival in miniature swine," *J Exp Med*. Nov. 1, 1984;160(5):1495–508.

Qin, L., et al., "Gene transfer for transplantation. Prolongation of allograft survival with transforming growth factor–beta 1," *Ann Surg*. Oct. 1994;220(4):508–18; discussion 518–9.

Qin, L., et al., "Retrovirus–mediated transfer of viral IL–10 gene prolongs murine cardiac allograft survival," *J Immunol*. Mar. 15, 1996;156(6):2316–23.

Raju, G.P., et al., "Prolongation of cardiac allograft survival with transforming growth factor–beta 1 in rats," *Transplantation*. Aug. 15, 1994;58(3):392–6.

Ramsdell, F. and Fowlkes, B.J., "Maintenance of in vivo tolerance by persistence of antigen," *Science*. Aug. 21, 1992;257(5073):1130–4.

Rocha, B., et al., "Clonal anergy blocks in vivo growth of mature T cells and can be reversed in the absence of antigen," *J Exp Med*. May 1, 1993;177(5):1517–21.

Roser, B.J., "Cellular mechanisms in neonatal and adult tolerance," *Immunol Rev*. Feb. 1989;107:179–202.

Sakaguchi, S., et al., "Immunologic self–tolerance maintained by activated T cells expressing IL–2 receptor alpha–chains (CD25). Breakdown of a single mechanism of self–tolerance causes various autoimmune diseases," *J Immunol*. Aug. 1, 1995;155(3):1151–64.

Seddon, B. and Mason, D., "The third function of the thymus," *Immunol Today*. Feb. 2000;21(2):95–9.

Shevach, E.M., "Regulatory T cells in autoimmmunity," *Annu Rev Immunol*. 2000;18:423–49.

Singer, A., et al., "Self recognition in allogeneic radiation bone marrow chimeras. A radiation–resistant host element dictates the self specificity and immune response gene phenotype of T–helper cells," *J Exp Med*. May 1, 1981;153(5):1286–301.

Snijdewint, F.G., et al., "Prostaglandin E2 differentially modulates cytokine secretion profiles of human T helper lymphocytes," *J Immunol*. Jun. 15, 1993;150(12):5321–9.

Starzl, T.E., et al., "Chimerism and donor–specific nonreactivity 27 to 29 years after kidney allotransplantation," *Transplantation*. Jun. 1993;55(6):1272–7.

Taams, L.S., et al., "Anergic T cells actively suppress T cell responses via the antigen–presenting cell," *Eur J Immunol*. Sep. 1998;28(9):2902–12.

Tomita, Y., et al., "Importance of suppressor T cells in cyclophosphamide–induced tolerance to the non–H–2–encoded alloantigens. Is mixed chimerism really required in maintaining a skin allograft tolerance?" *J Immunol*. Jan. 15, 1990;144(2):463–73.

Vendetti, S., et al., "Anergic T cells inhibit the antigen–presenting function of dendritic cells," *J Immunol*. Aug. 1, 2000;165(3):1175–81.

Verbanac, K.M., et al., "A role for transforming growth factor–beta in the veto mechanism in transplant tolerance," *Transplantation*. Mar. 27, 1994;57(6):893–900.

Wekerle, T., et al., "Anti–CD154 or CTLA4Ig obviates the need for thymic irradiation in a non–myeloablative conditioning regimen for the induction of mixed hematopoietic chimerism and tolerance," *Transplantation*. Nov. 15, 1999;68(9):1348–55.

Wilson, D.B., "Idiotypic regulation of T cells in graft–versus–host disease and autoimmunity," *Immunol Rev*. Feb. 1989;107:159–77.

Zheng, X.X., et al., "Administration of noncytolytic IL–10/Fc in murine models of lipopolysaccharide–induced septic shock and allogeneic islet transplantation," *J Immunol*. May 15, 1995;154(10):5590–600.

Pawelec, et al., "Cytokine Modulation of TH1/TH2 Phenotype Differentiation in Directly Alloresponsive CD4+ Human T Cells," Transplantation, 62(8):1095–1101 (Oct. 1996).

Zeha VI–Willner et al., "The Mitogenic Activity of Staphylococcal Enterotixin B (SEB): A Monovalent T Cell Mitogen That Stimulates Cytoloytic T Lymphocytes but Cannot Mediate Their Lytic Interaction," *Journal of Immunology* 127(8):2682–2687 (1986).

Zeller et al., Induction of CD4+ T Cell Alloantigen–Specific Hyporesponsiveness by IL–10 and TGF–$\beta^1$, *Journal of Immunology* 163:3684–3691 (1999).

Han, et al., "A New Type of CD4+ Suppressor T cell Completely Prevents Spontaneous Autoimmune Diabetes and Recurent Diabetes in Syngeneic Islet–Transplanted NOD Mice," *Journal of Autoimmunity*, 9:331–339 (1996).

Rook et al., "Effects of Transforming Growth Factor $\beta$ on the Functions of Natural Killer Cells: Depressed Cytolytic Activity and Blunting of Interferon Responsiveness," *J Immunology* 136(10):3916–3920 (1986).

Asai O, et al., "Suppression of graft–versus–host disease and amplification of graft–versus–tumor effects by activated natural killer cells after allogeneic bone marrow transplantation," *Journal of Clinical Investigation* 101(9):1835–1842 (1998).

Boussiotis, "Altered T–cell receptor + CD28–mediated singnaling and blocked cell cycle progression in interleukin 10 and transforming growth factor–β–treated alloreactive T cells that do not induce graft–versus–host disease," *Blood* 97:565–571 (Jan. 2001).

Koh et al., "Adoptive cellular immunotherapy: NK cells and bone marrow transplantation," *Histol Histopathol* 15:1201–1210 (2000).

Sykes, M. et al., "In Vitro And In Vivo Analysis Of Bone Marrow–Derived CD3+, CD4–, CD8–, NK1.1+ Cell Lines," Cell Immunol. 129(2):478–83 (1990).

* cited by examiner

METHOD TO PREVENT GRAFT REJECTION USING TGF-BETA TO INDUCE T SUPPRESSOR CELLS

This application is a continuing application of U.S. S. No. 60/196,446, filed Apr. 11, 2000.

FIELD OF THE INVENTION

The field of the invention is related to compositions and methods useful for preventing graft rejection in a recipient following organ transplantation.

BACKGROUND OF THE INVENTION

Figure 1:
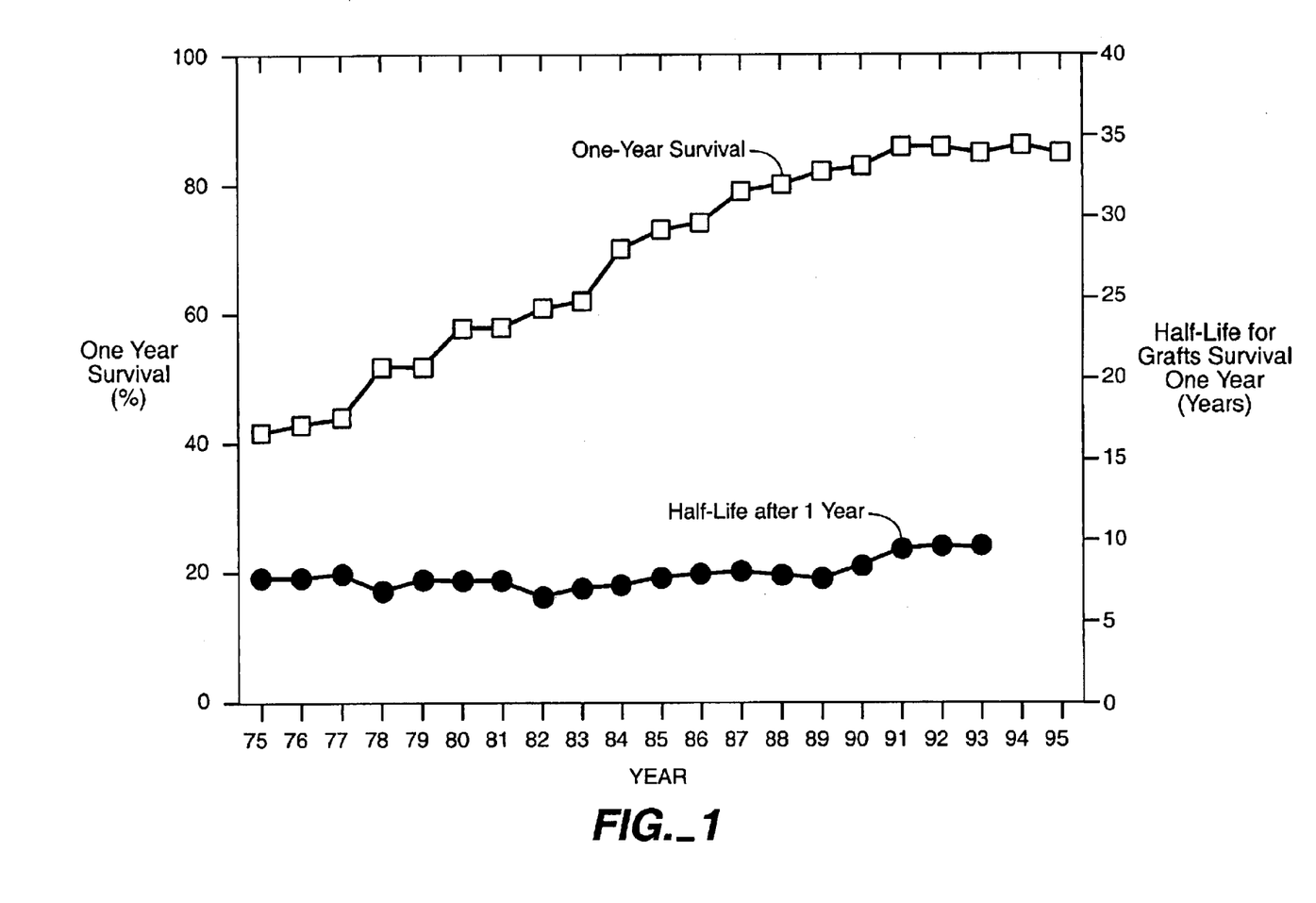
FIG. 1 depicts the lack of progress in preventing chronic rejection over the last twenty years.

Organ transplantation has been used to improve the quality of human life. Substantial progress has been made in the transplantation of kidneys, hearts, lung, livers and pancreas. Current immunosuppressive drugs are generally effective in blocking the immediate rejection of these organs. However, when the organ is from an unrelated donor, i.e., allograft, these drugs become less successful with the passage of time because immunosuppressive drugs are often ineffective in blocking chronic allograft rejection. In addition, there are significant side effects associated with long term immunosuppressive therapy. Each year approximately 10,000 kidney transplants are performed in the United States. While the chances that the graft will function well for at least one year have been increasing, there has been a lack of progress in preventing chronic allograft rejection during the past 20 years (See FIG. 1; In Fundamental Immunology, 4th ed., Paul, W. E. (ed.), Lippincott-Raven, Philadelphia, 1999, p. 1201). As a result, only 50% of transplants are still functioning years later. There is an urgent need, therefore, for new methods to prevent chronic rejection.

Graft rejection occurs when the immune system of the recipient recognizes foreign histocompatibility antigens. Infrequently, rejection is caused by antibodies, either preformed or the result of multiple blood transfusions. Rejection generally occurs when T lymphocytes from the recipient recognize and respond to donor histocompatibility antigens (Pescovitz M D, Thistlethwaite J R Jr, Auchincloss H Jr, et al. J Exp Med 1984;160:1495–1508).

There are two major histocompatibility complex (MHC) loci. Both major and minor histocompatibility antigens have been described as well as the genes that encode them. One encodes MHC class I antigens which are recognized by CD8+ T cells and another encodes MHG class II antigens which are recognized by CD4+ cells. MHC class I antigens are expressed on almost all tissues of the body. Both MHC I and II antigens are very polymorphic so that it is highly unlikely that antigens from unrelated individuals will be identical.

Differences in MHC antigens between donor and recipient trigger a strong immune response by the recipient which results in the rejection of the transplanted organ. Foreign MHC antigens are directly recognized by the recipient's immune cells and also indirectly recognized by antigen-presenting cells of the recipient which have processed donor MHC antigens. The classical model of allograft rejection emphasizes CD4+ T cells of the recipient recognizing MHC class II antigens of the donor. These activated CD4+ cells serve as helper cells for recipient CD8+ which are sensitized by direct recognition of donor MHC class I antigens. The activated CD8+ cells then kill donor cells by lysing them (Mizuochi T, Golding H, Rosenberg A S, Glimcher L H, Malek T R, Singer A. J Exp Med 1985;162:427–443. 205). Further studies have revealed additional participation of recipient antigen presenting cells, B cells, NK cells and NK T cells which adds complexity to the mechanisms responsible for graft rejection.

Graft destruction which occurs within the first few weeks after transplantation is called "acute rejection". Usually, the use of immunosuppressive drugs temporarily prevents this result. Unfortunately, the grafts may eventually fail weeks or months later. This failure is referred to as "chronic rejection." Both humoral and cellular mechanisms have been implicated in chronic rejection. Anti-donor antibodies have been claimed to promote chronic rejection, but this is controversial. It is generally believed that chronic rejection is the consequence of persistent sensitization of the immune system to donor MHC antigens. The immune cells of the recipients cannot "learn" to accept the donor MHC antigens as self and respond by attacking the graft.

There are two approaches to prevent graft rejection. The first is by treatment with non-specific immunosuppressants and the second is to induce donor-specific tolerance. The standard first approach is to use immunosuppressive drugs such as steroids, azathioprine, mycophenolate, cyclosporine, FK-506, rapamycin, leflunomide, or 15-deoxyspergualin. These drugs suppress immune responses by inhibiting lymphocyte gene transcription, cytokine signal transduction, nucleotide synthesis and cell differentiation. These drugs are associated with lifelong increased risks of infection and malignancy. In addition, anti-T cell antibodies such as anti-lymphocyte serum or anti-thymocyte globulin are also powerful immunosuppressants. However, they have major side effects include serum sickness and infectious complications More recently, OKT3, a mouse antibody directed against the CD3 antigen of humans, has become widely used in clinical transplantation. (Cosimi A B, Burton R C, Colvin R B, et al Transplantation 1981,32:535–539). Other monoclonal antibodies used include the antibody to the IL-2 receptor (anti-CD25) and the anti-ICAM-1 or anti-TNF-α to block the effector mechanism of graft rejection. These monoclonal antibodies also have broad toxic side effects.

The ultimate goal of transplantation immunology is to enable the recipient to become tolerant to donor histocompatibility antigens. That is, to prevent the recipient's immune cells from recognizing donor antigens (i.e., accepting the donor organ as "self") so that the graft is not rejected. The current state of the art in this area is reviewed herein and elsewhere (See Hugh Auchincloss, Jr., Megan Sykes, and David H. Sachs In Fundamental Immunology, 4th ed., Paul, W. E. (ed.), Lippincot-Raven, Philadelphia, N.Y., 1999 pp 1182–1222).

Tolerance can be achieved by three mechanisms. The first is "clonal deletion"; the elimination of lymphocytes which react to the donor antigens. The second is "clonal anergy"; the failure of T cells to proliferate in response to donor antigen. Anergy is generally reversible and can be reversed by infection or elimination of antigen (Rocha B, Tanchot C, Von Boehmer H. J Exp Med 1993;177:1517–1521) (Ramsdell F, Fowlkes B J. Science 1992;257:1130–1134). The third is "suppression"; which can be either non-specific or antigen-specific. Non-specific suppression can result from the secretion of soluble molecules that inhibit immune function. Suppressive molecules include prostaglandins (Snijdewint F G M, Kalinski P, Wierenga E A, Bos J D, Kapsenberg M I. J Immunol 1993;150:5321–5329, Betz M, Fox B S. J Immunol 1991;146:108–113), nitric oxide (Langrehr J M, Dull K E, Ochoa J B, et al. Transplantation 1992;53:632–640), and cytokines (Verbanac K M, Carver F M, Haisch C E, Thomas J M. Transplantation 1994;57:893–900); Raju G P, Belland S E, Eisen H J. Transplantation 1994;58:392–396).

Certain T cells, called "suppressor cells", produce inhibitory cytokines which include IL-4, IL-10, and TGF-β which, non-specifically, block graft rejection (Qin L, Chavin K D, Ding Y, Woodward J E, Favaro J P, Lin J, Bromberg J S. Ann Surg 1994;220:508–519); (Qin L, Chavin K D, Ding Y, et al. J Immunol 1996; 156:2316–2323); (Zheng X X, Steele A W, Nickerson P W, Steurer W, Steiger J, Strom T B. J Immunol 1995;154:5590–5600). The existence of alloantigen-suppressor cells have been reported (Pearce N W, Spinelli A, Gurley K E, Hall B M. Transplantation 1993;55:374–379; Roser B J. Immunol Rev 1989; 107:179–202; Tomita Y, Mayumi H, Eto M, Nomoto K. J Immunol 1990;144: 463–473), but these cells are difficult to clone (Koide J, Engleman E G. J Immunol 1990;144:32–40).

Naturally occurring suppressor T cells produced by the thymus have been characterized in mice. These are CD4+ cells that express CD25, cell surface IL-2 receptor a chains (Shevach, E. A. (2000) Annu. Rev. Immunol. 18:423–449; Seddon, B., and D. Mason, (2000) 21.95–99; Sakaguchi, S., N. Sakaguchi, M. Asano, M. Itoh, and M. Toda, (1995) J. Immunol. 155:1151–1164). To date, this T cell subset has not been well described in humans and whether these cells can be expanded in the periphery is unknown.

CD4+ cells repeatedly stimulated with IL-10 or activated with immature dendritic cells develop down-regulatory activity (Groux, H., A. O'Garra, M. Bigler, M. Rouleau, S. Antojejko, J. E. De Vries, and M. G. Roncarolo, (1997) Nature. 389:737–742; Jonuleit, H., E. Schmitt, G. Schuler, K. Jurgen, and A. H. Enk. (2000) J Exp Med 192:1213–1222). These T cells, called TR1 or TR1-like cells, are anergic and their immunosuppressive effects are mediated by IL-10 and TGF-β. Anergic T cells suppress other T cell responses by targeting antigen-presenting cells (Taams, L. S., A. J. M. L. van Rensen, M. C. M. Poelen, C. A. C. M. van Els, A. C. Besseling, J. P. A. Wagenaar, W. van Eden, and M. H. M. Wauben (1998) Eur J Immunol 28:2902–2912; Vendetti, S., J. G. Chai, J. Dyson, E. Simpson, G. Lombardi and R. Lechler, (2000), J. Immunol. 165:1175–1181). Unfortunately, large numbers of these cells are required for suppressive activity and their capacity to expand is very poor.

The profile of cytokines produced by T cells can affect the survival of an organ graft. The shift in T cell response from the pro-inflammatory Th1 response (IL-2 and IFN-γ) to the anti-inflammatory Th2 (IL-4, IL-10) response has been associated with allograft acceptance (Roser B J. Immunol Rev 989: 107:179–202; Lancaster F, Chui Y L, Batchelor J R. Nature 1985;315:336–337; Wilson. Immunol Rev 1989;107:159–176). Only limited data, however, implicate an active role of Th2 cells in tolerance induction (Bucy R P, Li J, Huang G Q, Honjo K, Xu X Y. [Abstract]. FASEB J 1995;9:A497; Wilson. Immunol Rev 1989;107:159–176). Moreover, in some cases Th2 cells can mediate or contribute to graft rejection.

Methods to specifically direct T cells to become tolerant or produce inhibitory cytokines would be very helpful in promoting the survival of transplanted organs. Several tolerance-inducing strategies have been attempted in combination with conventional immunosuppressive drugs. In rodents, tolerance can be achieved by giving a dose of lethal irradiation to a mouse, and saving the animal by giving back T cell-depleted syngeneic and allogeneic bone marrow cells. The hematopoietic cells that repopulate the animal will display histocompatibility antigens of both donor and recipient cells and, therefore, will be tolerant to grafts from each mouse strain (Singer A, Hathcock K S, Hodes R J. J Exp Med 1981;153:1286). Non-myeloablative conditioning regimens have been described where mice are sublethally irradiated, T cell depleted with monoclonal antibodies and given either anti-CD154 or CTLA4lg which block co-stimulatory molecules (Wekerle, 1999). This strategy achieves central tolerance and should have long lasting effects, but has not yet been performed in large animals. None of these strategies have been used to replace chronic therapy in clinical transplantation.

Peripheral tolerance can be achieved by blocking co-stimulatory molecules. The combination of CTLA4lg and anti-CD154 markedly prolongs the survival of primary skin allografts in mice (Larsen C P, Elwood E T, Alexander D Z, et al. Nature 1996;381:434–438; Kirk A D, Harlan D M, Armstrong N N, et al. Proc Natl Acad Sci USA 1997;94:8789–8794). A major problem with strategies to block co-stimulatory molecules is that they cannot prevent generation of new T cells in the recipient capable of recognizing donor antigens.

There are examples of solid organ transplants that have survived for many years in human recipients who did not receive hematopoletic cell transplants (Starzl T E, et al. (1993) Transplantation, 55:1272–1277). In these instances, passenger leukocytes from the graft might emigrate to the thymus and tolerize subsequently developing thymocytes. The heavy doses of immunosuppressive drugs used to prevent acute rejection blocks this thymic education. Strategies to reduce the dosage of immunosuppressive therapy might overcome this problem and lead to long lasting central tolerance.

An ideal strategy to prevent graft rejection would be to induce T cells to develop the capacity to suppress the immune attack by the recipient against donor histocompatibility antigens. Although CD4+ cells repeatedly activated in the presence of IL-10 develop potent suppressor activity, these cells have a very short life span and poor proliferative potential (Groux H, et al., (1997) Nature, 389:737–42). Thus, there is a need for a method to generate suppressor T cells which are hardy and able to proliferate.

SUMMARY OF THE INVENTION

In accordance with the objects outlined above, the present invention provides compositions and methods that can be used to induce T cell tolerance in a solid organ transplant recipient. The compositions include compounds that inhibit or suppress immune function by inducing a population of T cells to develop suppressor activity. Compounds useful in the compositions of the invention include anti-inflammatory cytokines, such as IL4, IL-10 and TGF-β, chemokines, prostaglandins and nitric oxide.

In an additional aspect, the present invention provides methods of inhibiting graft rejection in a recipient comprising removing peripheral blood mononuclear cells (PBMC) from a donor and recipient, culturing the donor and recipient cells together in the presence of a compound that induces T cell suppressor activity, and administering these treated cells to the recipient following graft transplantation In a further aspect, the invention uses closed systems for the purification, conditioning and expansion of T cell populations before administering them to a patient.

BRIEF DESCRIPTION OF THE DRAWINGS

One way allogenic mixed lymphocyte reaction (MLR) is used to generate regulatory T cells that suppress cytotoxic T cell activity. In allogeneic MLR, T cells from one individual (i.e., A) are mixed with cells from an unrelated individual (i.e., B). In the absence of regulatory T cells which suppress cytotoxic T cell activity individual A's T cells recognize B's cells as foreign and develop the capacity to kill B's cells.

Regulatory T cell subsets that prevent this killing are generated from A by negative selection by staining the cells with appropriate monoclonal antibodies and using immunomagnetic beads to remove the stained cells. The resulting T cell subsets are cultured for five days with cells from B in the presence of TGF-β. Controls consist of T cells cultured with stimulator cells in the absence of TGF-β.

The effect of TGF-β conditioned T cell subsets on allogeneic MLR was determined by mixing regulatory cells to effector cells in a ratio of 1:4. After five days of culture with stimulator cells from B, the cytotoxic activity of T cells from A was determined using a standard chromium release assay in which effector cells from A were mixed with chromium labeled lymphoblasts from B in the effector to target cell ratios shown. Chromium release was measured in a 4 hour assay (open squares). Control T cell subsets cultured with stimulators in the absence of TGF-β are indicated by open circles. T cell subsets cultured with stimulator cells in the presence of TGF-beta are shown as closed circles. In all experiments, TGF-beta enhanced the capacity of the T cell subsets to suppress the generation of cyotoxic activity.

FIG. 5 depicts suppression of lymphocyte proliferation by regulatory CD4+ T cells induced with TGFP-β. Naive CD4+ T cells from A were mixed with stimulator cells as described above and added to fresh responder and stimulator cells at the indicated ratios. The bars show the mean uptake of tritiated thymidine ±SEM after 7 days of culture. The lightly shaded bar (Nil) indicates the proliferative response of the responder T cells without added CD4+ cells. The darkly shaded bar indicates the effect of control CD4+ cells cultured with stimulator cells, but without TGF-β. The black bar indicates the effect of CD4+ cells cultured with stimulator cells in the presence of TGF-β (1 ng/ml). The effect of these CD4+ cells on the proliferative response of fresh responder cells added to irradiated stimulator cells after 7 days of culture is shown.

FIG. 6 depicts the potency of CD4+ regulatory T cells induced by TGF-β and shows that they express CD25. Naive CD4+ T cells primed with irradiated allogeneic stimulator cells ±TGF-β (1 ng/ml) and CD4 regulatory cells were separated into CD25+ and CD25− fractions by cell sorting.

FIG. 8 depicts the proliferative response of CD4+ regulatory T cells to alloantigens. Naive CD4+ T cells and irradiated stimulator cells ($1 \times 10^6$/ml) were cultured ±TGF-β for 5 days in serum free medium to generate CD4+ regulatory T cells. The cells were washed and rested for 3 days in culture medium containing 10% normal human serum. The cells were labeled with carboxyfluorescein (CFSE) and re-stimulated with irradiated allogeneic stimulator cells. The intensity of CFSE staining after three and five days 5 days of culture is shown. The heavy line shows CD4 regulatory cells and the thin line CD4+ cells primed with alloantigens without TGF-β. The proliferative response of the CD4+ cells primed with TGF-β is stronger than that of control CD4+ cells. Similar results have been obtained in four other experiments.

DETAILED DESCRIPTION OF THE INVENTION

The present invention makes possible the transplantation of solid organs such as kidneys, heart, lungs, liver and pancreas in humans using methods to prevent chronic graft rejection. By mixing large numbers of T cells ex vivo with a compound that induces suppressor activity, a population of suppressor or regulatory T cells is produced. Suppressor cells can be administered to a recipient before, at the time of, or after the transplant to prevent the recipient's T cells from killing donor cells, thereby inducing tolerance and long term survival of the transplant. The particular advantage of this procedure is that the immune system of the recipient is harnessed to perform a function that conventional and experimental therapies have failed to achieve.

Thus, the present invention prevents graft rejection by suppressing T cell activation and inducing a tolerant state in the recipient's cells. This is achieved by inducing some of the recipient's cells to assume a surveillance role and prevent other recipient cells from mounting an immune attack against the graft. The net effect is for the recipient's lymphocytes to become tolerant of the histocompatibility antigens of the donor, thereby making possible the long term survival of the graft.

This strategy is unlike almost all other treatment therapies currently in use because cells, rather than organ recipient as a whole, are treated with potent pharmacologic agents. Thus, the recipient is spared from the severe side effects associated with these agents.

An advantage of the present invention is that it may reduce or minimize the need to administer highly toxic immunosuppressive medicines that must be given to recipients of organ transplants. In the present invention, the recipient's own immune cells are induced to suppress the immune response, thus, the doses of toxic immunosuppressive drugs administered for this purpose can be reduced.

Thus, the present invention provides a lowered probability of serious side effects as only trace amounts of compounds which may block the immune response are returned to the recipient.

The present invention shows that a population of a recipient's T cells can be induced to block an immune attack against the donor organ. Without being bound by theory, it appears that there are several ways the methods of the invention may work, either alone or in combination. First, recipient cells may be activated to become tolerant to the donor cells. Second, recipient cells may be activated to assume a surveillance role and prevent other recipient cells from killing donor cells. Third, treatment of recipient cells with a suppressive compound may inhibit the cytotoxic activity of some recipient T cells by inducing other recipient cells to have suppressor activity. For example, in FIGS. 2–4, TGF-$\beta$ is used to induce various T cell subsets to have suppressor activity and prevent lysis of donor cells. Suppressing the lysis of donor cells by recipient cells will decrease or eliminate chronic graft rejection.

Accordingly, the present provides compositions and methods of inducing T cell tolerance in an organ transplant recipient. The present invention provides methods comprising removing peripheral blood mononuclear cells (PBMCs) from both a recipient and a donor, mixing the recipient and donor cells together, and treating the cells with a regulatory composition to generate a population of suppressor T cells. These suppressor T cells can be introduced into a recipient at the time of transplant, or at various times thereafter to prevent chronic graft rejection.

By "recipient" herein is meant a human which is to receive an organ transplant. In some case, the recipient may be an animal, including but not limited to rodents including mice, rats, and hamsters, domestic animals, wild animals and primates. Likewise, for the purpose of the invention, a "donor" is a human or animal from which the organ is obtained.

The present invention is directed to methods utilized in organ transplant. By "organ" herein is meant solid organs such as kidneys, heart, lungs, liver, and pancreas In a preferred embodiment, rejection of the transplanted organ is prevented by inducing tolerance in a recipient's T cells by administering T cells conditioned to become suppressor cells. By "tolerance" or "T cell tolerance" or grammatical equivalents herein is meant immune non-responsiveness to donor cells, i.e., a tolerance to the histocompatibility antigens of the donor. That is, abolishment of cytotoxic T cell activity by recipient cells against donor cells. Preferably, the recipient's T cells retain the ability to recognize other antigens as foreign, to facilitate tumor killing and general immunological responses to foreign antigens.

T cells are conditioned to become suppressor cells by treatment with a regulatory composition. A regulatory composition includes at least one compound which induces T cells to develop suppressive activity. By "suppressive activity" herein is meant at least some of the treated T cells develop the capacity to prevent cytotoxic T cell activity in other T cells.

T cells which develop the capacity to block cytotoxic T cell activity are referred to herein as "suppressor T cells" or "regulatory T cells." By "suppressor T cells" herein is meant a population of T cells which develop the capacity to inhibit other T cells from killing donor cells.

Using methods outlined herein, graft rejection is decreased or eliminated. By "decreased" or "eliminated" herein is meant that at least one symptom of graft rejection is ameliorated. This may be evaluated in a number of ways, including both objective and subjective factors on the part of the patient as is known in the art. The clinical pattern of organ dysfunction often helps to suggest the diagnosis of rejection. However, no clinical sign can definitively diagnose rejection. Although it would be useful to determine a means of identifying rejection episodes based on systemic manifestations of the immunologic mechanisms involved, there is not yet a well-established assay to measure rejection activity (Paul, W. E. (1999) Fundamentals of Immunology).

The methods provide for the removal of blood cells from recipients and donors. In general, peripheral blood mononuclear cells (PBMCs) are taken from recipients and donors using standard techniques. By "peripheral blood mononuclear cells" or "PBMCs" herein is meant lymphocytes (including T-cells, B-cells, NK cells, etc.) and monocytes. As outlined more fully below, it appears that the main effect of the regulatory composition is to enable CD4+ T cells and/or other T cell subsets (i.e., CD8+ T cells, NK T cells, gamma delta T cells) to develop suppressive activity. Accordingly, the PBMC population should comprise CD4+ T cells. Preferably, only PBMCs are taken, either leaving or returning red blood cells to the patient. This is done as is known in the art, for example using leukophoresis techniques. In general, a 5 to 7 liter leukopheresis step is done, which essentially removes PBMCs from a patient, returning the remaining blood components. Collection of the cell sample is preferably done in the presence of an anticoagulant such as heparin, as is known in the art.

In general, the sample comprising the PBMCs can be pretreated in a wide variety of ways. Generally, once collected, the cells can be additionally concentrated, if this was not done simultaneously with collection or to further purify and/or concentrate the cells. The cells may be washed, counted, and resuspended in buffer.

The PBMCs are generally concentrated for treatment, using standard techniques in the art. In a preferred embodiment, the leukopheresis collection step results a concentrated sample of PBMCs, in a sterile leukopak, that may contain reagents or doses of the regulatory composition, as is more fully outlined below. Generally, an additional concentration/purification step is done, such as Ficoll-Hypaque density gradient centrifugation as is known in the art.

In a preferred embodiment, the PBMCs are then washed to remove serum proteins and soluble blood components, such as autoantibodies, inhibitors, etc., using techniques well known in the art. Generally, this involves addition of physiological media or buffer, followed by centrifugation. This may be repeated as necessary. They can be resuspended in physiological media, preferably AIM-V serum free medium (Life Technologies) (since serum contains significant amounts of inhibitors of TGF-$\beta$) although buffers such as Hanks balanced salt solution (HBBS) or physiological buffered saline (PBS) can also be used.

Generally, the cells are counted; approximately from $1 \times 10^9$ to $2 \times 10^9$ white blood cells are collected from a 5–7 liter leukopheresis step. These cells are brought up in roughly 200 mls of buffer or media.

In a preferred embodiment, the PBMCs may be enriched for one or more cell types. For example, the PBMCs may be enriched for CD8+ T cells, CD4+ T cells or NK T cells. This is done as is known in the art, as described in Gray et al. (1998), *J. Immunol.* 160:2248, hereby incorporated by reference. Generally, this is done using commercially available immunoabsorbent columns, or using research procedures (the PBMCs are added to a nylon wool column and the eluted, nonadherent cells are treated with antibodies to CD4, CD16, CD11b, and CD74, followed by treatment with immunomagnetic beads, leaving a population enriched for CD8+ T cells). In one embodiment, cell populations are enriched for CD4+ cells, as these appear to be the cells most useful in the methods of the invention.

In a preferred embodiment, the CD4+ cells could be further purified to include only undifferentiated, naive cells. This is done by depleting them of CD45 RO+ cells using monoclonal antibodies. This procedure eliminates populations of CD4+ cells which may have acquired functions which might interfere with the generation or activity of suppressor T cells.

In other embodiments, CD8+ cells, CD3+CD4−CD8− cells, or NK T cells may be treated with a regulatory composition to develop suppressor activity.

Once the cells have undergone any necessary pretreatment, the cells are treated with a regulatory composition. By "treated" in this context herein is meant that the cells are incubated with the regulatory composition for a time period sufficient to result in T cell tolerance, particularly when transplanted into the recipient patient. The incubation will generally be under physiological temperature.

By "regulatory composition" or "tolerance composition" is meant a composition that can induce T cell tolerance to donor histocompatibility antigens. The regulatory composition will include irradiated T cell-depleted mononuclear cells from the donor to limit the suppressor T cells to only those which can react with the histocompatibility antigens of the donor and at least one compound which induces these activated T cells to become suppressor cells.

The concentration of the regulatory composition will vary depending on the identity of the compounds included in the composition, but will generally be at physiologic concentration, i.e. the concentration required to give the desired effect, i.e. an enhancement of specific types of regulatory cells.

Donor blood cells are obtained by pheresis and after removal of red blood cells, $1-2 \times 10^9$ PBMC are treated with anti-T-cell antibodies, such as anti-CD3 antibodies and the positive T cells removed by immuno-magnetic beads. The T cell-depleted donor cells are irradiated to prevent them from proliferating and mixed with the recipient cells at a ratio of 0.01 to 10, with from about 0.1 to 3 per donor cells being preferred, 0.5 to 2:1 being especially preferred, and 1:1 being ideal.

Compounds used to activate T cells to become suppressor cells include, but are not limited to, prostaglandins, nitric oxide, chemokines and cytokines. In a preferred embodiment, the compound used to activate T cells is a cytokine.

In a preferred embodiment, cytokines, such as interleukin 2 (IL-2), interleukin 15 (IL-15), interleukin 4 (IL-4), interleukin 10 (IL-10) and transforming growth factor beta (TGF-β) are used to activate T cells.

A composition containing more than one compound may be used to activate T cells to become suppressor cells. The compositions may contain more than one compound from the same class of compounds. i.e., two or more cytokines, chemokines, or prostaglandins may be mixed together. The composition also may contain compounds from different classes of compounds, such as a cytokine and a chemokine, or a cytokine and a prostaglandin, etc.

In a preferred embodiment, compositions containing two or more cytokines are used to activate T cells. For example, IL-2 and TGF-β are mixed together to increase the generation of suppressor cells.

In a preferred embodiment, TGF-β is used to generate suppressor T cells. By "transforming growth factor "β" or "TGF-β" herein is meant any one of the family of the TGF-βs, including the three isoforms TGF-β1, TGF-β2, and TGF-β3; see Massague, (1980), *J. Ann. Rev. Cell Biol* 6:597. Lymphocytes and monocytes produce the β1 isoform of this cytokine (Kehrl et al. (1991), *Int J Cell Cloning* 9:438–450). The TFG-β can be any form of TFG-β that is active on the recipient cells being treated. In humans, recombinant TFG-β is currently preferred. A human TGF-β2 can be purchased from Genzyme Pharmaceuticals, Farmington, Mass. In general, the concentration of TGF-β used ranges from about 10 pg to about 5 ng/ml of cell suspensions, with from about from about 0.1 ng to 3 ng/ml being preferred, and 1 ng/ml being ideal.

TGF-β is incubated with the recipient cells and a population of irradiated donor PBMC (harvested as outlined above). The donor cells are irradiated so that they cannot attack the recipient cells. The incubation period occurs for a period of time sufficient to cause an effect, generally from 4 hours to 5 days although both shorter and longer periods are possible.

In a preferred embodiment, treatment of recipient cells with the regulatory composition is followed by expansion of these cells before transfer to the recipient patient.

In other embodiments, it may be desirable to transfer the cells instead of expand the cells. In this case, the cells are transferred immediately after washing to remove the regulatory composition, and frozen or otherwise stored.

Once the cells have been treated, they may be evaluated or tested prior to transplantation into the recipient. For example, a sample may be removed for: sterility testing; gram staining, microbiological studies; LAL studies; mycoplasma studies; flow cytometry to identify cell types; functional studies, etc. These and other lymphocyte studies may be done before and after treatment. A preferred analysis is to label donor cells; incubate the treated tolerant recipient cells with the labeled population to verify that the recipient cells are tolerant and will not kill the donor cells.

Figure 2A:
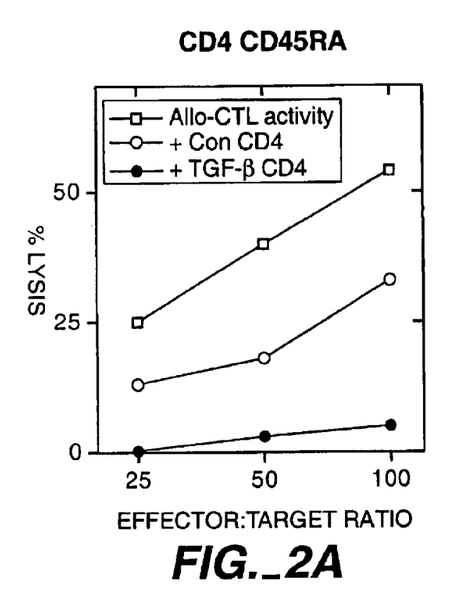
FIG. 2 depicts the effect of TGF-β on T cell subsets in the generation of cells that suppress cytotoxic T cell activity.
Figure 2B:
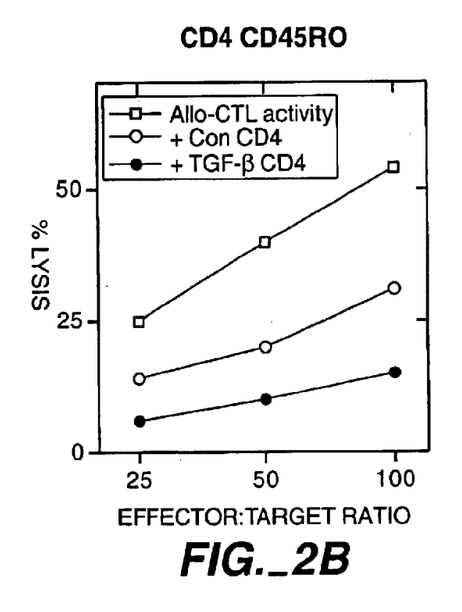
Figure 2C:
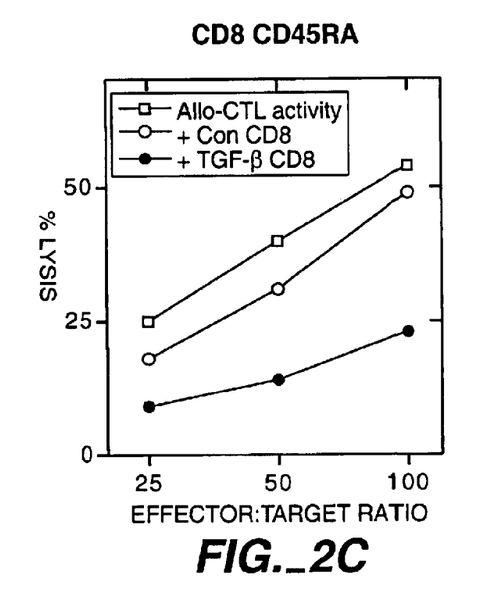

Assays such as those shown in FIG. 2, can also be used to determine if the regulatory composition has induced suppressor cells. This is done by mixing suppressor cells generated ex vivo with the recipient's T cells and assaying the survival of the donor cells.

In a preferred embodiment, the treatment results in the conditioning of the T cells to become non-responsive to histocompatibility cells of the donor so that graft rejection is prevented In a preferred embodiment, the isolation of T cells, conditioning them with the regulatory composition, and expansion of these cells are performed in a closed system such as the Nexell Isolex 300 system to minimize the introduction of toxins to the product.

The recipient's treated T cells are transferred back to the recipient patient. This is generally done as is known in the art, and usually comprises injecting or introducing the treated cells into the recipient as will be appreciated by those in the art. This may be done via intravascular (IV)

administration, including intravenous or intraarterial administration, intraperitoneal administration, etc. For example, the cells may be placed in a 50 ml Fenwall infusion bag by injection using sterile syringes or other sterile transfer mechanisms. The cells can then be immediately infused via IV administration over a period of time, such as 15 minutes, into a free flow IV line into the patient. In some embodiments, additional reagents such as buffers or salts may be added as well.

After reintroducing the cells into the patient, the effect of the treatment may be evaluated, if desired, as is generally outlined above and known in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

TGF-β Activated CD4+ T Cells Suppress Cytotoxic T Cell Activity

Blood from both donor and recipient were obtained by pheresis. PBMC from each individual were separated from RBC using the Nexell Isolex 500 closed system. CD4+ cells from the recipient and T cell-depleted mononuclear cells from the donor were prepared using commercially available reagents.

If the recipient receives an organ transplant from a donor whose mononuclear cells are not available, the recipient's T cells are conditioned with irradiated mononuclear cells from a pool of donors which express a broad panel of common and uncommon histocompatibility antigens.

Recipient CD4+ cells were cultured with irradiated donor mononuclear cells in the presence of TGF-β for 5 days. The CD4+ cells which react with donor cells in the presence of TGF-β were induced to become suppressor T cells. The cells were incubated with donor alloantigens or mitogens for an additional 10 days to expand the number of suppressor T cells.

To test the potency of these suppressor T cells, they were cultured for 5 days with the recipient's T cells mixed with donor irradiated non-T cells to induce killer T cells. The recipients T cells are then mixed with chromium labeled donor lymphoblast cells and incubated for 4 hours. If the donor cells are killed by the recipients cytotoxic T cells, chromium is released into the culture medium. By determining the amount of chromium released, the percentage of cells killed can be determined.

Figure 3A:
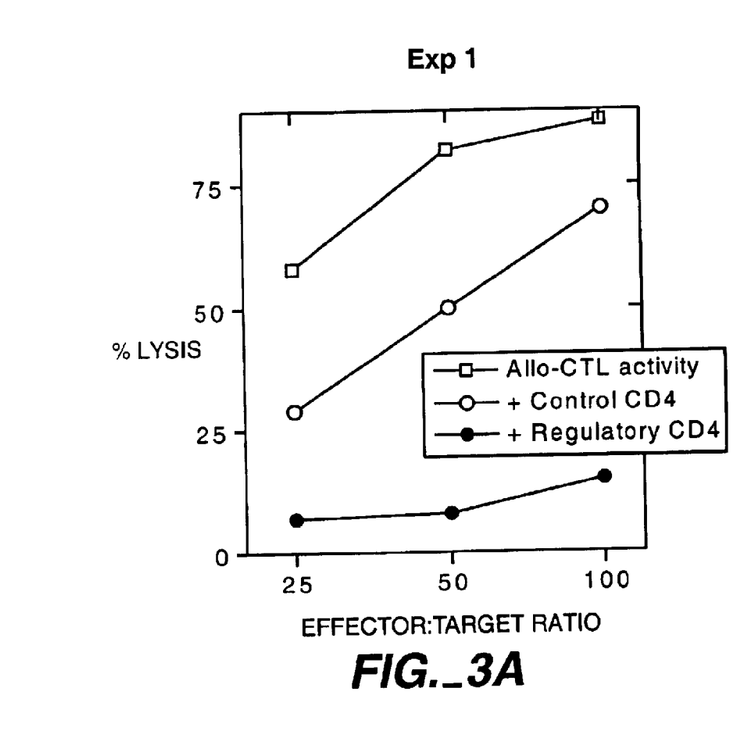
FIG. 3 depicts two independent experiments showing the regulatory effects of TGF-β on CD4 CD45RA T cells cultured with stimulator cells in the presence or absence of TGF-β. Control CD4 CD45RA cells cultured with stimulator cells in the absence of TGF-β have modest to moderate suppressive activity. In contrast, T cells primed with TGF-β 1 ng/ml markedly suppress or abolish allo-CTL activity.
Figure 3B:
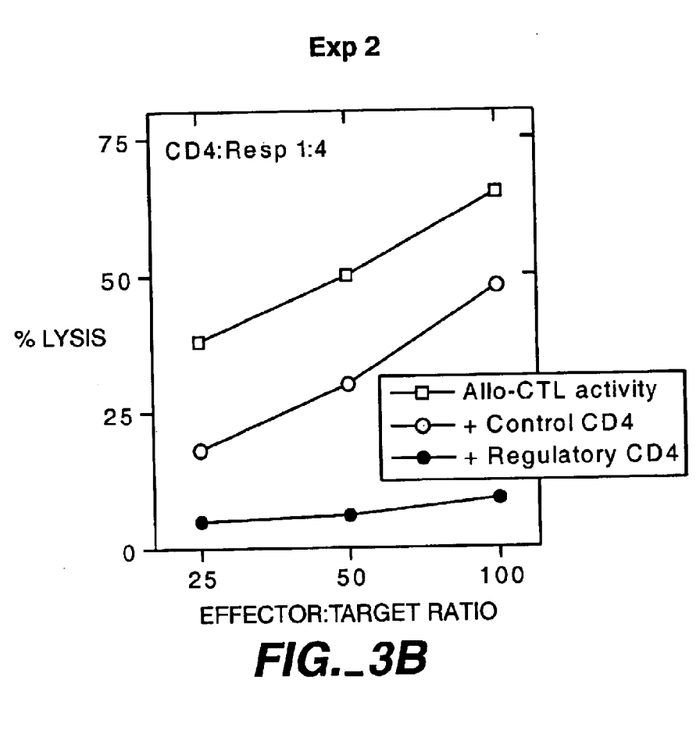
Figure 4A:
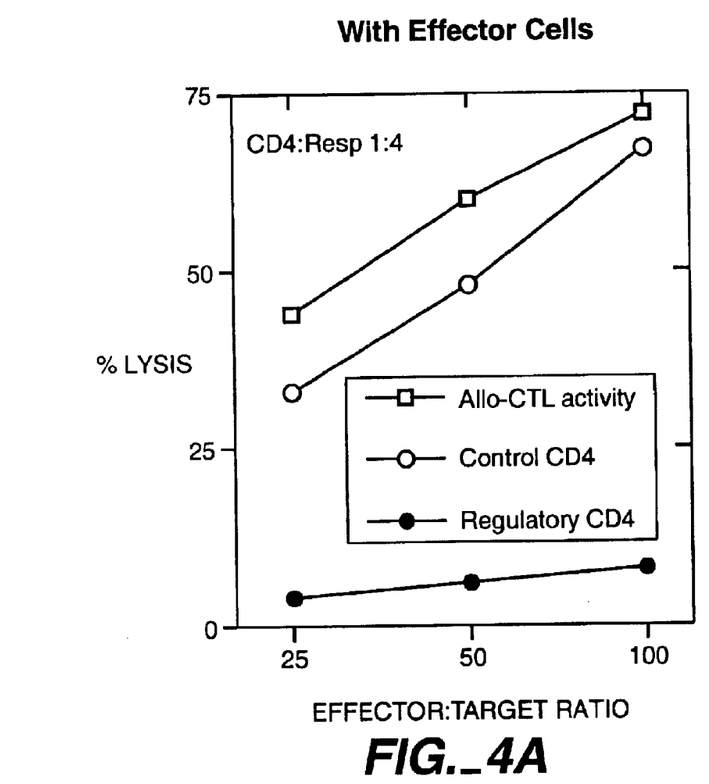
FIG. 4 depicts that CD4 suppressor cells require cell contact to inhibit cytotoxic T cell activity. In these experiments, regulatory CD4 cells from CD4 CD45 RA were conditioned with TGF-β as described in FIGS. 2 and 3. An aliquot of the cells was mixed with responder T cells from A and stimulator cells from B. A separate aliquot of regulatory cells was separated from the responder and stimulator cells by a membrane. The results indicate that suppressor T cells require cell contact to exert their regulatory effects.
Figure 4B:
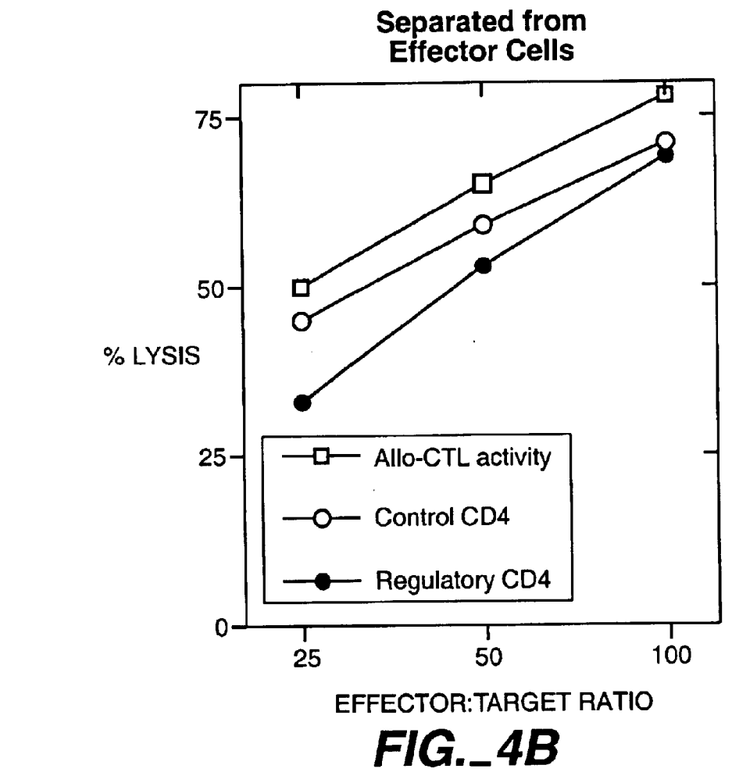
Figure 5:
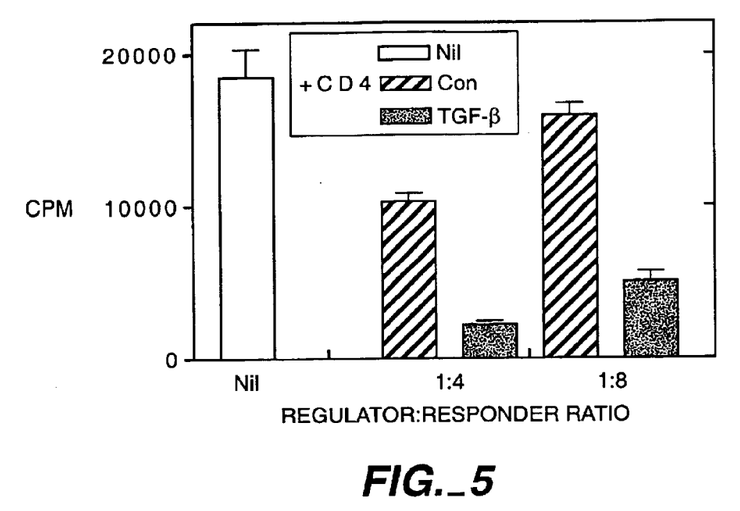
Figure 6A:
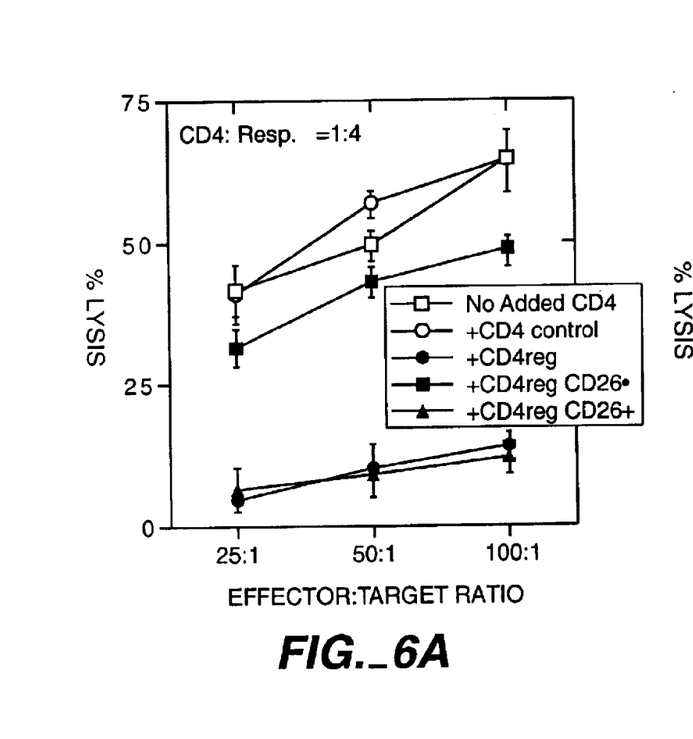
FIG. 6A depicts the effect of primed CD4+ cells mixed with fresh T cells at a 1:4 ratio. The suppressive activity is concentrated in the CD25 fraction.
Figure 6B:
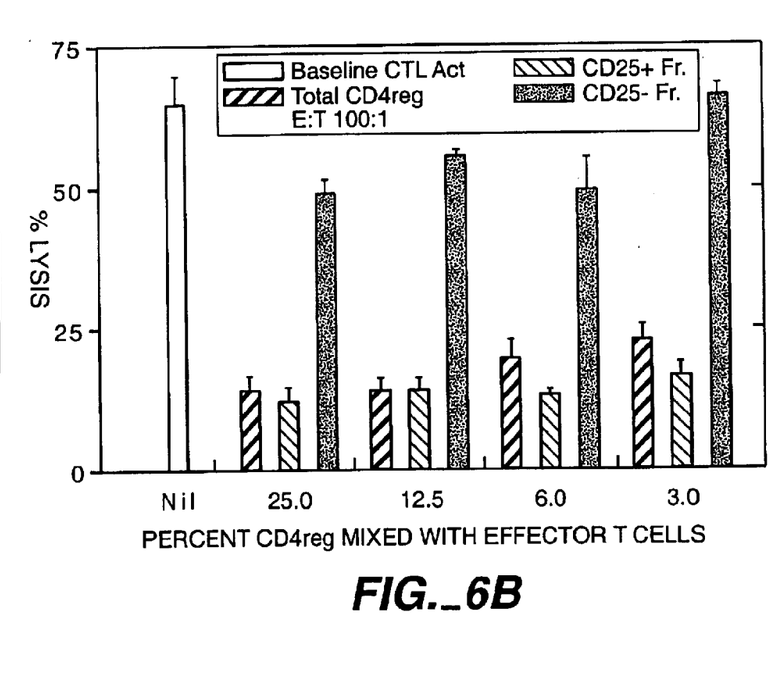
FIG. 6B depicts the effect of various dilutions of these primed CD4+ T cells added to fresh responder cells on the generation of CTL activity. Results shown were performed at an effector to target cell ratio of 100:1. Significant suppressive activity was present when less than 1 CD4 reg was mixed with 100 responder T cells.
Figure 7A:
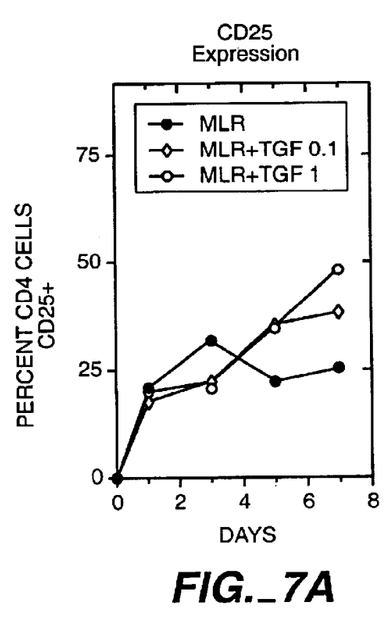
FIG. 7 depicts the effects of a regulatory composition on the expression of CD25 and CTLA-4 by CD4+ cells. The T cell subset was prepared from the spleens of DBA/2 mice. The CD4+ cells were cultured with irradiated allogeneic splenic lymphocytes from C57BL/6 mice with and without TGF-β (0.1–1 ng/ml) for the days shown. The cells were stained for CD25 or CTLA-4 and the percentage of cells expressing the respective markers was determined by flow cytometry. By day 5 the presence of TGF-β significantly enhanced expression of CD25 and CTLA-4.
Figure 7B:
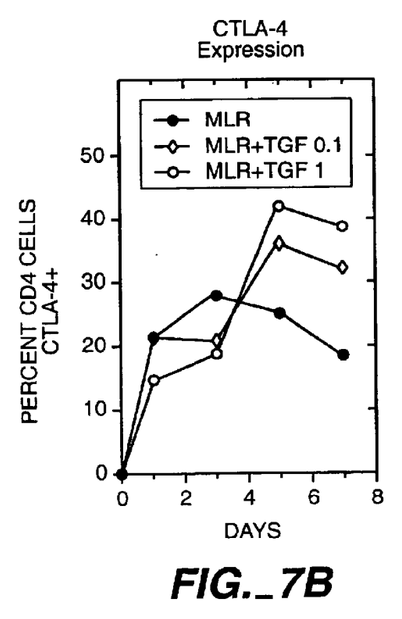
Figure 8A:
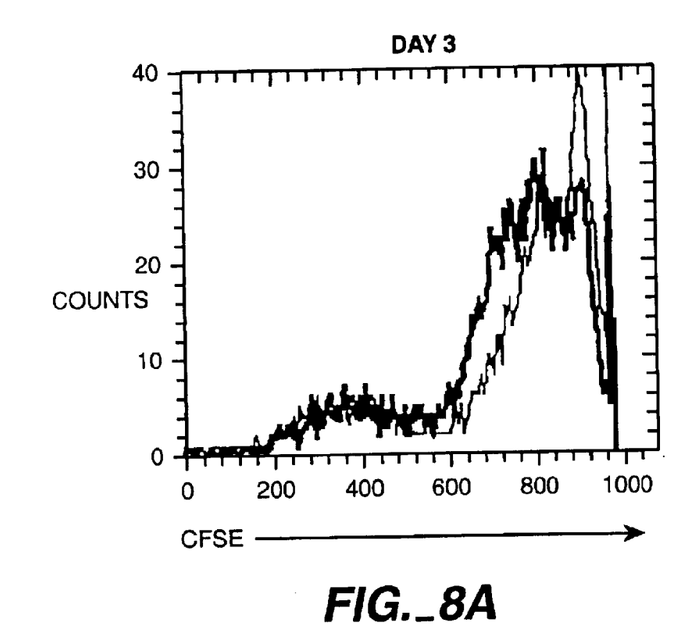
Figure 8B:
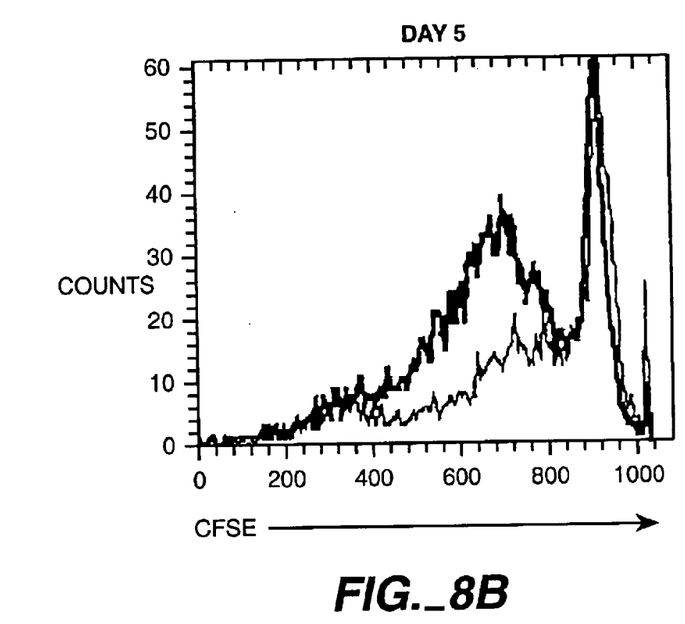

FIGS. 2–4 show that regulatory T cells generated with TGF-beta block the ability of the recipient's T cells to kill donor T cells.

In the standard cytotoxic assays shown in FIGS. 2–4, recipient cells were cultured with labeled donor cells in 25:1, 50:1 and 100:1 ratios. These combinations of recipient and donor cells are called effector to target ratios. Killing is indicated by the various symbols. As expected, maximum killing was seen at the highest effector to target ratio. CD4+ cells cultured with donor stimulator cells had a modest inhibitory effect. CD4+ cells that had been conditioned with TGF-β 1 ng/ml almost completely abolished the capacity of recipient T cells to kill donor mononuclear cells.

Example 2

TGF-β Activated T Cells Suppress Cytotoxic T Cell Activity

Blood from both donor and recipient were obtained by pheresis PBMC from each individual were separated from RBC using the Nexell Isolex 500 closed system. T cells from the recipient which contain both the major subsets (CD4+ and CD8+cells) and the minor subsets (TNK cells and gamma delta T cells), and T cell-depleted mononuclear cells from the donor were prepared using commercially available reagents.

Recipient T cells were cultured with irradiated donor mononuclear cells in the presence of TGF-β for 3 to 5 days. The various T cell subsets which react with donor cells in the presence of TGF-β were induced to become suppressor T cells. Similar procedures were repeated for an additional 10 days to expand the number of suppressor T cells The recipient's T cells primed with donor alloantigens in the presence of TGF-beta are then tested for suppressive activity by showing that they prevent recipient's precursor killer cells from developing the capacity to kill donor T cells by the procedures described in Example 1.

Example 3

Treatment of T Cells From a Recipient of Kidney Graft From a Non-Identical Sibling Donor to Prevent Graft Rejection CD4+ cells conditioned with 1 ng/ml TGF-β, are transferred to the recipient 1 day before kidney transplant and allowed to "home" to lymphoid tissue. These CD4+ cells circulate to the recipient's lymphoid organs, where they block the recipient's T cell response to donor histocompatibility antigens. As a result, the recipient's T cells become tolerant to the donor's histocompatibility antigens. This tolerance reduces acute rejection, lessening the need for high doses of immunosuppressive drugs. As the recipient's lymphocytes are "educated" to develop long lasting tolerance, chronic rejection is decreased or eliminated. If signs of graft rejection recur, additional infusions of regulatory T cells will ameliorate this response.

What is claimed is:

1. A method for decreasing graft rejection of a solid organ by a recipient comprising:

a) isolating peripheral blood mononuclear cells (PBMC) from a recipient and an organ donor;

b) irradiating T cell-depleted mononuclear cells from said organ donor PBMC;

c) combining ex vivo said recipient PBMC with said population of donor irradiated T cell-depleted mononuclear cells with a regulatory composition comprising TGF-β to induce a population of recipient suppressor T cells;

d) expanding said population of recipient suppressor T cells; and e) administering said recipient suppressor T cells to said recipient.

2. The method according to claim 1 wherein said regulatory composition further comprises cytokines selected from the group consisting of IL-2 and IL-15.

3. The method according to claim 1, wherein said PBMC from said recipient are enriched for CD4+ T cells.

4. The method according to claim 3 wherein said CD4+ cells are enriched for naive CD4+ T cells.

5. The method according to claim 1, wherein said PBMC from said recipient are enriched for CD8+ T cells.

* * * * *